United States Patent [19]

Marchosky et al.

[11] Patent Number: 4,947,842
[45] Date of Patent: Aug. 14, 1990

[54] METHOD AND APPARATUS FOR TREATING TISSUE WITH FIRST AND SECOND MODALITIES

[75] Inventors: Jose A. Marchosky, Creve Couer; Christopher J. Moran, Town & Country, both of Mo.; Neal E. Fearnot, West Lafayette, Ind.

[73] Assignee: Medical Engineering and Development Institute, Inc.

[21] Appl. No.: 310,541

[22] Filed: Feb. 13, 1989

Related U.S. Application Data

[63] Continuation-in-part of Ser. No. 247,769, Sep. 22, 1988, which is a continuation-in-part of Ser. No. 193,167, May 2, 1988, which is a continuation-in-part of Ser. No. 112,628, Oct. 22, 1987, abandoned, which is a continuation-in-part of Ser. No. 697,697, Feb. 4, 1985, Pat. No. 4,719,919, which is a continuation of Ser. No. 459,708, Jan. 21, 1983, abandoned.

[51] Int. Cl.$^5$ .............................................. A61F 7/12
[52] U.S. Cl. .................................... 128/401; 606/28
[58] Field of Search ........ 128/303.1, 303.12, 399–402, 128/24 A, 24.1; 604/114, 164, 265; 606/27, 28

[56] References Cited

U.S. PATENT DOCUMENTS

| | | | |
|---|---|---|---|
| 3,698,394 | 10/1972 | Piper et al. | 128/303.1 |
| 3,833,003 | 9/1974 | Taricco | 604/164 |
| 3,884,220 | 5/1975 | Hartnett | 604/51 |
| 4,591,496 | 5/1986 | Cohen et al. | 424/15 |
| 4,638,045 | 1/1987 | Kohn et al. | 530/323 |
| 4,692,152 | 9/1987 | Emde | 604/265 |
| 4,693,556 | 9/1987 | McCaughan | 128/303.1 |
| 4,744,933 | 5/1988 | Rha et al. | 264/4.3 |
| 4,749,620 | 6/1988 | Rha et al. | 428/402.2 |
| 4,808,157 | 2/1989 | Coombs | 604/44 |

OTHER PUBLICATIONS

Yatvin et al., "Temperature- and pH-Sensitive Liposomes for Drug Targeting," *Methods in Enzymology*, vol. 149, pp. 77–87, 1987.

Heller J., "Use of Polymers in Controlled Drug Release," *Biocompatible Polymers, Metals, and Composites*, Technomic Publishing Co., Inc., Lancaster, PA, 1983, Ch. 24, pp. 551–584.

Hornback, Ned B., "Hyperthermia and Cancer," (CRC Press, Inc., Boca Raton, Fla., 1984), vol. I, pp. 65–75, 95–107; vol. II, pp. 107–111, 131–133.

Song et al., "Heat and Blood Flow," *Annals New York Academy of Sciences*, pp. 45–47.

Storm, F. Kristian [Ed.], *Hyperthermia in Cancer Therapy*, (G. K. Hall Medical Publishers, Boston, 1983), Chapters 1, 2, 11 and 12.

Nussbaum, Gilbert H. [Ed.], *Physical Aspects of Hyperthermia*, (American Institute of Physics, New York, 1982), pp. 90–104, 280–356, 368–392, and 495–538.

*Primary Examiner*—Max Hindenburg
*Attorney, Agent, or Firm*—Richard J. Godlewski

[57] ABSTRACT

Method and apparatus is disclosed for treating tissue interstitially with multiple modalities of treatment. The apparatus comprises a semi-rigid elongated member that is implanted interstitially in the malignant tumor. A hollow passageway is longitudinally positioned in the member for positioning one or more modalities inserted or positioned therein. The elongated member is coated with another modality such as a carrier substance that is responsive at a temperature above normal tissue temperature for releasing a carried substance such as a therapeutic anti-cancer drug. Within the elongated member, an electrical heater element for one modality produces heat when energized for heating the probe, the carrier substance, the anti-cancer drug, and the surrounding tissue. A second modality such as a source of radiation is inserted in the passageway after the probe is interstitially implanted. A trocar stylet is initially inserted in the passageway to implant the probe. When the probe is implanted, the trocar stylet is removed, and the heater element and/or source of radiation is inserted into the passageway. The several modalities combine in a synergistic manner to provide an overall treatment that has an effectiveness level greater than the sum of the individual modalities.

24 Claims, 7 Drawing Sheets

METHOD AND APPARATUS FOR TREATING TISSUE WITH FIRST AND SECOND MODALITIES

CROSS-REFERENCE TO RELATED APPLICATIONS

This application is a continuation-in-part of application Ser. No. 247,769, filed Sept. 22, 1988, pending, which is a continuation-in-part of application Ser. No. 193,167, filed May 2, 1988, pending, which is a continuation of application Ser. No. 112,628, filed Oct. 22, 1987, abandoned, which is a continuation-in-part of application Ser. No. 697,697, filed Feb. 4, 1985, Pat. No. 4,719,919, which is a continuation of application Ser. No. 459,708, filed Jan. 21, 1983, abandoned.

TECHNICAL FIELD

This invention relates to method and apparatus for the treatment of tissue and particularly to the combined use of at least two different modalities in the treatment of cancerous tissue.

BACKGROUND OF THE INVENTION

Present modalities of treatment for malignant tumors and particularly malignant brain tumors include amongst others surgery, radiation therapy, and chemotherapy. However, the treatment of malignant brain tumors has a very poor prognosis for survival. Furthermore, the quality of life of survivors during and after treatment is typically poor. Clinical evidence indicates that hyperthermia treatment with modest increases in the temperature of cancerous tissue cells has led to the regression, disappearance, and on some occasions cure of malignant tumors. Hyperthermia is more cytotoxic to neoplastic cells than normal cells, because neoplastic cells are oxygen deprived, nutritionally deficient, and low in pH making them incapable of tolerating the stress imposed by elevated temperature.

The major forms of energy for generating hyperthermia presently include microwaves, radio frequency induction, radio frequency localized current, and ultrasound. Most of the techniques used to dispense these are non-invasive, i.e., the heat generating source is external to the body and does not invade the body. Several problems exist with these non-invasive techniques. First, the energy must pass through the skin surface, and, as a result, a substantial amount of power is absorbed by normal body tissue. One consequence is severe skin burns. Second, these external heating sources cause nonuniform temperature profiles throughout the tumor and increased temperatures in normal tissue. Nonuniform heating does not assure destruction of the tumor at cold spots. Whereas, unwanted destruction of normal tissue may occur at hot spots.

Studies indicate that tumor mass reduction by hyperthermia is related to the thermal dose. Thermal dose is the minimum effective temperature applied throughout the tumor mass for a defined period of time. Hot spots and cold spots which occur with microwave hyperthermia may cause increased cell death at the hot spots, but ineffective treatment at cold spots results in future tumor growth.

Others have attempted the use of interstitial techniques to obtain local hyperthermia, with limited success. Interstitial heating of brain tumors through an implantable microwave antenna has been investigated. However, microwave probes are ineffective in producing precisely controlled heating of tumors. Temperature may deviate as much as 10 degrees Celsius from the desired target temperature. Besides, microwave activity adversely affects cellular structures and their integration, regardless of other thermal effects. The result is, again, nonuniform temperatures throughout the tumor. Such variations are a result of the microwave antenna's inability to evenly deposit energy throughout the tissue.

Efferent blood flow is a major cause of heat loss for tumors being heated, and blood flow varies throughout the tumor. As a result, uneven heating results even if energy is delivered uniformly throughout the volume of the tumor. To be effective, the application and deposition of thermal energy to the tumor must be precisely controlled to compensate for the variations in blood flow. In addition, the therapy itself will perturb the tumor's vascular system during treatment causing variations in local perfusion around the probe. Thus, heat loss from a tumor will be time dependent and affected by the hyperthermia treatment. This demonstrates the need to both monitor and control the temperature in multiple regions of the tumor throughout treatment.

Another brain tumor treatment, chemotherapy, also has a number of problems. The perfusion of agents from the blood to brain cells is much lower than that from the blood to other cells. This phenomenon, commonly known as the blood-brain barrier, prevents chemotherapeutic agents from effectively treating brain tissue having neoplastic cells. Increasing the concentration levels of these agents in blood, however, does not necessarily result in increased delivery of these agents to the tumor site. Another problem is the damage to normal tissue. This problem is, of course, weighed against the effects of unchecked tumor growth. In addition, the side effects of these high concentration level agents in the patient typically create a poor quality of life during and after treatment. Still another problem is the effective life of the agent, which may be as short as 15 to 20 minutes. Getting a short life agent intravenously to a brain tumor in a timely manner and for an extended period of time complicates the delivery process. Controllably releasing an agent in a cyclical manner further complicates the process.

Studies have shown that elevating the temperature of various chemotherapeutic drugs only a few degrees Celsius increases the effectiveness level of the drug significantly. The added benefits of treating a malignant tumor with these drugs at temperatures elevated above normal body temperatures are significant. However, a major problem is delivering these drugs while either maintaining the temperature thereof at a controlled elevated level for any extended period of time or raising the temperature of the drug to the control level once delivered to the tumor site.

Radiation therapy is another modality available for treating cancer. Radiation therapy has the disadvantage of killing healthy as well as cancerous tissue in the exposed area. For brain tumor regression, radiation therapy is perhaps the most effective treatment. However, as a result of radiation treatments at levels adequate for tumor remission, radiation necrosis, a self-destruction of normal brain tissue, renders patients mentally and physically nonfunctional with symptoms similar to Alzheimer's disease.

Studies have shown that such modalities of treatment have limited degrees of success when provided singly. These studies have also indicated that the effectiveness level of radiation therapy is elevated when provided concomitantly with other treatment modalities such as chemotherapy and hyperthermia, thereby providing synergistic effects.

SUMMARY OF THE INVENTION

The foregoing problems are solved and a technical advance is achieved with illustrative apparatus for treating tissue interstitially with multiple modalities of treatment. The apparatus includes an elongated member with a distal end for implanting the member interstitially in tissue such as a malignant brain tumor. A hollow passageway is longitudinally positioned in the member for positioning a first modality in the member for providing a first treatment of the tissue. Illustratively, this first modality would include an electrical heater element that is inserted in the passageway of the interstitially implanted member for providing a hyperthermia treatment of the surrounding tissue. Positioned about the distal end of the member is a second modality of the apparatus which is responsive to or interactive with the first modality for providing a second treatment. Illustratively, the second modality is a chemotherapeutic agent such as a chemotherapeutic drug whose effectiveness level is advantageously increased in response to the heat produced by the heater element.

The apparatus also includes a stylet insertable into the passageway for implanting the member interstitially in the tissue. The member also has an aperture therein for inserting the stylet into the passageway. After the distal end of the member is interstitially implanted in the tissue, the stylet is removed from the passageway to facilitate the insertion or provision of the first modality.

As previously suggested, the first modality includes a heater element such as an electrical conductive heater, a microwave or radiofrequency heater, fluid heater, and the like. As an alternative, the first modality includes a source of radiation such as iridium seeds that are positioned into the passageway with an insertable member for providing brachytherapy. The radiation also increases the effectiveness level of the second modality including, for example, chemotherapy or hyperthermia treatment. Another alternative for the first modality includes an injectable substance such as another chemotherapeutic agent or reactant that interacts with the second modality.

To further increase the effectiveness level of the overall treatment, a third modality is added to the first and second modalities. The third modality is at least responsive to one of the first and second modalities for increasing the effectiveness level of the third modality. Illustratively, first and second modalities of heat and radiation treatment are positioned in or about the passageway of the member that is coated with a chemotherapeutic agent. The coating agent is a third modality responsive to the heat and/or radiation for advantageously increasing the effectiveness level of the chemotherapeutic agent.

The method of the invention involves treating tissue with first and second modalities and optionally a third modality. The method comprises implanting an elongated member interstitially in the tissue and positioning a first modality in a passageway longitudinally positioned in the member. The method further comprises providing a second modality positioned about the distal end of the member when implanted interstitially in the tissue in response to the first modality.

The implanting includes positioning a stylet in the passageway and inserting the distal end of the member interstitially in the tissue with the stylet therein. The stylet advantageously guides or aids the implanting of the member interstitially in the tissue and is subsequently removed from the passageway for positioning a modality such as a heater element or source of radiation therein. Alternatively, both a heater element and a source of radiation are simultaneously positioned therein, comprising first and third modalities.

The second modality in response to at least one of the first and third modalities releases a drug at a temperature above a temperature of the tissue for providing a second treatment. The effectiveness level of the drug is advantageously increased in response to at least one of the first and third modalities. In addition, the effectiveness level is advantageously increased over the use of only two modalities. Considering a first modality of heat, a second modality of chemotherapy and a third modality of radiation, these three modalities in combination are synergistic.

DETAILED DESCRIPTION

Figure 1:
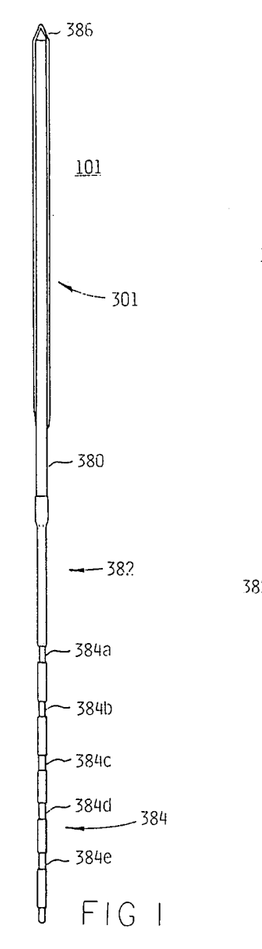
FIGS. 1 and 2 are side views of an illustrative probe.
Figure 2:
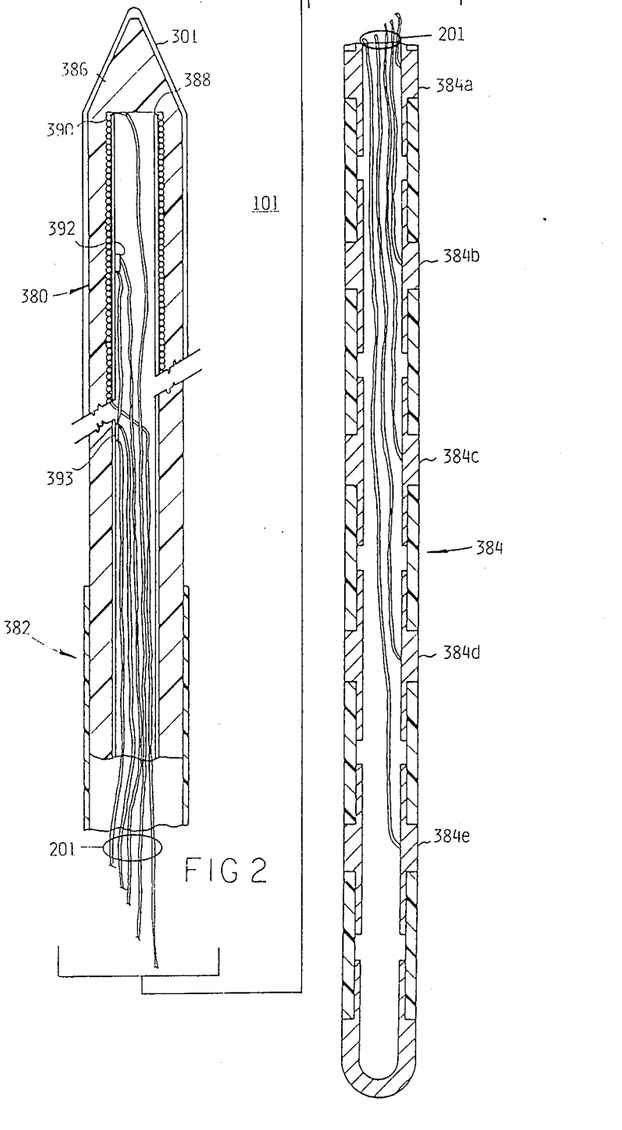

Depicted in FIGS. 1 and 2 is a probe 101, also referred to as a catheter, for interstitially implanting into tissue having malignant neoplastic (cancer) cells such as a malignant brain tumor. The implantable probe consists of a semi-rigid portion 380 which is directly implanted into the tumor, a flexible portion 382 which remains outside the body, and a connector portion 384 for mating to a manifold connector (not shown). The manifold connector in turn connects to a control system (not shown) which energizes a wire-wound heater element 390 that is positioned within the elongated member portion 380. An illustrative hyperthermia system including the manifold connector and control system are described in U.S. patent application, Ser. No. 193,167, filed May 2, 1988, of the present inventors, which is herein incorporated by reference. In addition, the control system monitors the temperature of the probe, as well as the surrounding tissue, and the power delivered thereto for maintaining a minimum temperature throughout the tissue which the probe is implanted therein. The semi-rigid portion of the probe is coated with an outer or coating substance layer 301, including a carrier and a carried substance. The carrier substance transports molecules of the carried substance such as a therapeutic drug within its molecular structure and also adheres to the outer surface of the semi-rigid portion. When the probe is implanted in the tissue, the carrier substance releases at a predetermined temperature, typically above 37° C., the therapeutic drug to the tissue having the neoplastic cells. The release of the carried substance or the rate at which it is released is controlled by any one or more of several factors including contact with the fluids of the tissue and the application of heat to the carrier substance from the heater element of the probe. Furthermore, the application of heat to the malignant tumor is also used to provide a second form of treatment.

Semi-rigid elongated member portion 380 has been designed to give the proper rigidity for insertion balanced with the desired flexibility for long term implantation. The flexible portion 382 prevents injury to the tissue adjacent to the probe by minimizing torque transmission from the manifold connection. The probe has been designed with the smallest possible diameter to minimize disturbance of tissue, displacement or destruction of important structures, and injury to blood vessels and yet large enough to adequately conduct heat with acceptable surface temperatures. The tip 386 of the probe has been tapered so that the tip selects a point of penetration into the tissue and the rest of the probe follows the same path, minimizing distortion of tissue and injury to the blood vessels.

Coating layer 301 substantially covers semi-rigid portion 380 and includes a carrier substance for releasing a carried substance to the tissue in which the probe is implanted therein. The carried substance is any drug, chemotherapeutic agent, synthesizer, inhibitor of chemical activities, enzyme, catalytic agent, or any other substance that when released in the interstitium into which the probe is implanted, will effect the tissue in a desired or beneficial manner. Furthermore, the carried substance may also comprise an anesthetic or analgesic for relieving pain. An anesthetic or analgesia is particularly helpful to relieve pain in the treatment of tumors in particularly sensitive areas such as the breast.

By way of one example, the carrier substance is any type of carrier molecule or compound that adheres to or joins with the surface of the probe without chemically interacting or bonding with the molecules of the probe or the carried substance. In one case, the carried substance is first applied to the surface of the probe, and then the carrier substance is applied to cover or coat the carried substance layer. In another case, a solution of the carried and carrier substances are mixed and applied to the outer surface of the probe. After application, the mixture dries in place on the surface of the probe. In such example, the carrier substance is selected from a group consisting of well-known and commercially available carbohydrates, fatty acids, proteins, nucleotide, or any other organic substance that can adhere to the surface of the probe as well as transport the molecules of the carried substance without chemically interacting or bonding therewith. When heat is applied, the carrier substance will either melt, peel off, disintegrate, or break down (i.e., by hydrolysis or bond cleavage), thereby releasing the carried substance interstitially to the tissue. One characteristic of the carrier substance is that the molecular structure of this adherent gradually allows release of the molecules of the carried substance for which it is acting as a carrier. By regulating the temperature of the probe, the duration of the heat application, or a combination of both, a graded release of the carried molecules is obtained. By way of a second example, the carrier substance comprises a compound or molecules that attach or chemically bond to the carried substance and the surface of the probe. Illustratively, one end of the carrier molecule attaches or bonds to the surface of the probe, and the other end (or multiple ends) attaches or bonds to a carried substance molecule. With the application of heat, the carrier molecule releases the carried molecule by a simple unfolding of the attaching end of the molecule by hydrolysis or bond cleavage of the carried molecule. In such second example, the carrier substance is selected from a group consisting of well-known and commercially available polypeptides, proteins, carbohydrate chains, fatty chains, or a mixture thereof such as glycoproteins.

By way of a third example, the carrier substance comprises a microcapsule. The outside surface of the microcapsule adheres or attaches to the surface of the probe, whereas the inner surface of the microcapsule adheres or attaches to the carried substance molecules. When heat is applied, the microcapsule either opens, dissolves, or melts thereby releasing the carried substance interstitially to the tissue. The microcapsule carrier substance is selected from a group consisting of polypeptides, proteins, carbohydrates, glycoproteins, or fatty acid substances. Presently, microencapsulation technology has been better developed for fatty acid chains. The advantage of fatty acid chains is that by changing the number of carbon atoms in the chain, the temperature at which a fatty acid (lipid) membrane melts or dissolves is readily controlled. Microcapsules of the same substance can be made of different sizes with different melting temperatures so that the timed release of the carried substance is controlled by varying the temperature of the applied heat. This is particularly advantageous when treatments are cyclical and occur over an extended period of time. Different carrier substances are used to form different types or sizes of microcapsules which permit not only the transport of different types and sizes of carried substances, but also control the release of the carried substances in time and space by varying the temperature of the applied heat.

A fourth example of the carrier substance is a well-known micropore membrane covering a probe with a layer of the carried substance already adhered thereto. The application of heat releases the carried substance from the surface of the probe. When released, the carried substance diffuses through the micropore membrane with the tissue fluid. The micropore membrane may also be combined with microcapsules to provide a broad range of release periods and temperatures.

In another example, the micropore membrane substantially covers the entire length of the elongated member. The member includes a port through which carried substances are injected between the membrane and the outer surface of the probe.

Figure 9:
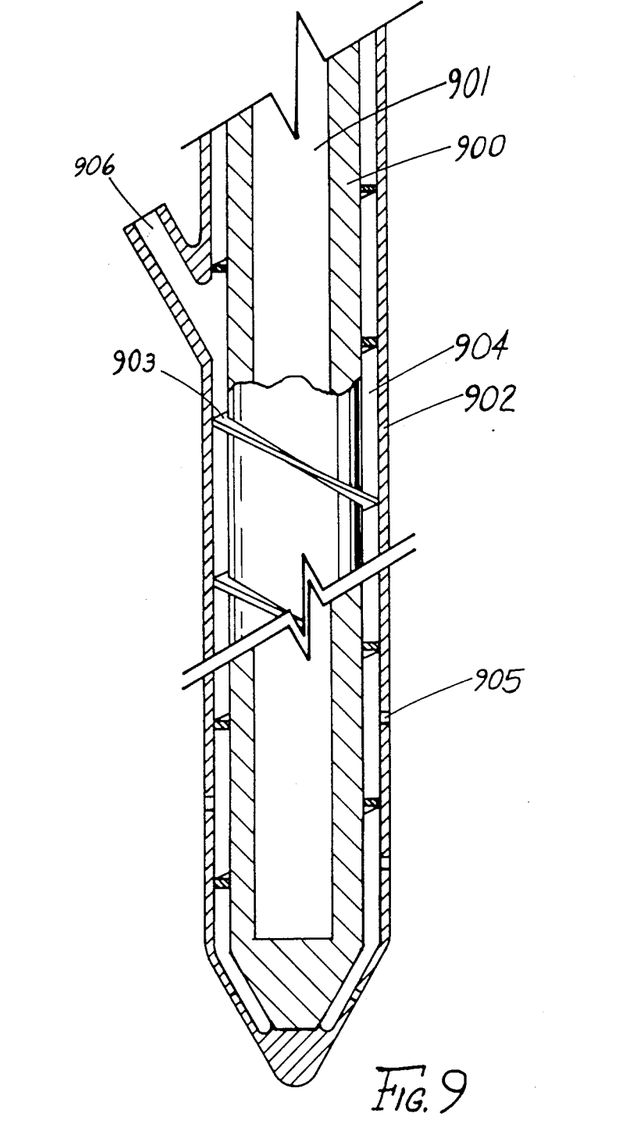
FIG. 9 is a view of yet another embodiment of the illustrative apparatus of this invention.

In yet another example, a plastic sheath surrounds the semi-rigid portion with a spacer therebetween to facilitate the injection of a therapeutic substance therein by way of a side port as shown in FIG. 9. The sheath may also comprise any number of other materials such as for directly diffusing, leeching, or time releasing the substance to the surrounding tissue.

Depicted in FIG. 3 is an enlarged view illustrating coating layer 301 and a cross section portion of semi-rigid portion 380. As shown in FIG. 3(*a*), molecules 302 of the carried substance are simply suspended by molecules 303 of the carrier substance which adheres to the outer surface of semi-rigid portion 380. One example of providing this coating layer is to mix an aqueous solution of the carrier and carried substance such as a carbohydrate and a therapeutic drug, dipping the semi-rigid portion of the probe in the solution, removing the probe with the solution thereon, and allowing the solution to dry thereby forming the desired coating layer.

Figure 3A:
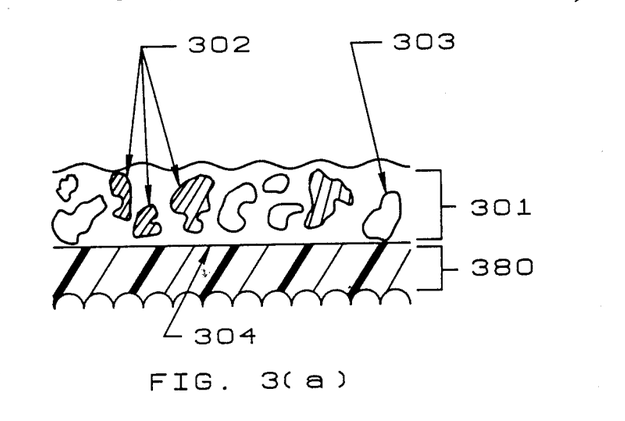
FIGS. 3(a)-(e) show sectional views of the outer or coating layer on the surface of the probe of FIG. 1.
Figure 3B:
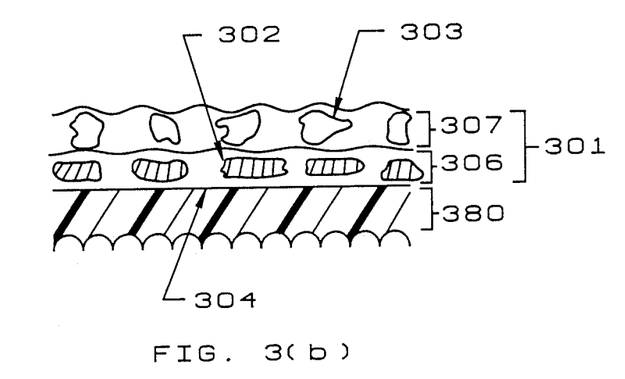

As shown in FIG. 3(b), molecules 302 of the carried substance form a layer 306 which adheres to outer surface 304 of semi-rigid portion 380 of the probe. One method of forming carried substance layer 306 is to dip semi-rigid portion 380 into a solution of the carried substance, removing the solution of the carried substance, and allowing the solution to dry in situ thereby forming layer 306. A similar technique is employed to form layer 307 of carrier substance molecules 303 covering carried substance layer 306.

Figure 3C:
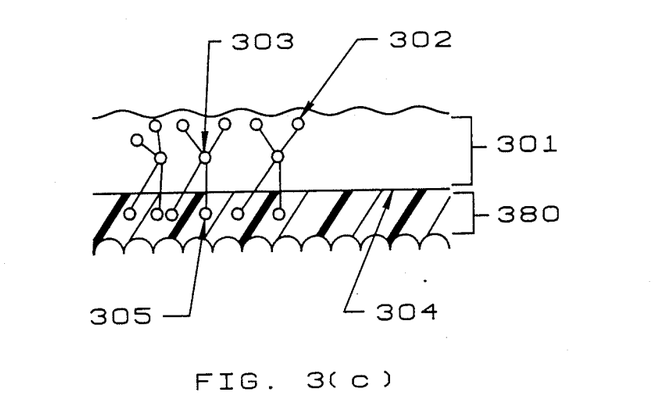

As shown in FIG. 3(c), the carrier molecules 303 are chemically bonded or linked to molecules 305 of semi-rigid portion 380 and molecules 302 of the carried substance. As shown, carrier agent molecules 302 link to molecules 303 of semi-rigid portion 380 thereby attaching coating layer 301 to outer surface 304 of the semi-rigid portion. Furthermore, carrier agent molecules 303 are also linked to carried substance molecules 302 for delivering the carried substance to the affected tissue when the probe is implanted therein. The carrier agent is selected to be biocompatible with the brain and other bodily tissues. Other desired characteristics of the carrier substance is that it should be nonantigenic, biodegradable, non-active biologically, and have a dense adhesion to the surface of the semi-rigid portion. It is also desirable that the carrier substance be mechanically friction (rub) resistant and should withstand a sterilization process.

One example of linking carrier agent molecules are monoclonal antibodies that form antigen-antibody/poison links. The antibody is linked to a chemotherapeutic agent such as ricin. The antibody is genetically formed to link to the cancer antigen. Cellular attachment links the agent (ricin) to the cancer cells causing selective death of only the cancer cells.

Figure 3D:
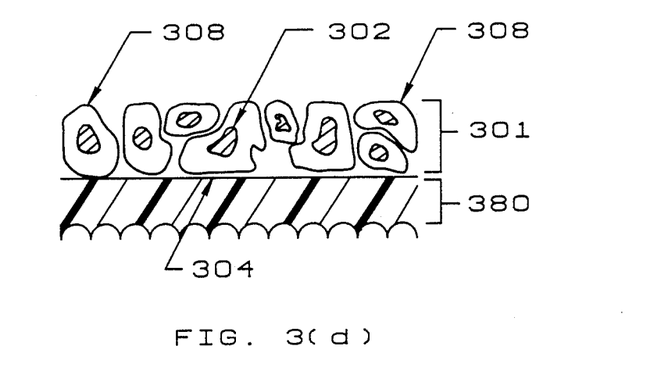

As shown in FIG. 3(d), well-known and commercially available carrier substance microcapsules 308 form layer 301. The outside surface of each microcapsule adheres or attaches to surface 304 of the probe. Carried substance molecules 302 adhere or attach to the inside surface of the microcapsule. When heated to a temperature above normal tissue temperature, the microcapsules open releasing the carried substance to the tissue. Nitrosourea BCNU (carmustine) is one example for use as the carried substance in the microcapsules.

Figure 3E:
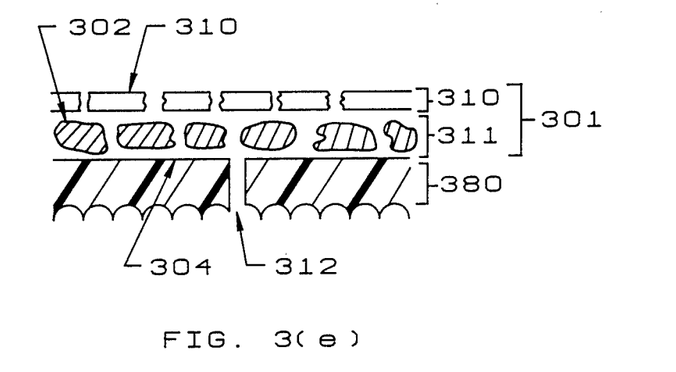

As shown in FIG. 3(e), well-known and commercially available carrier substance micropore membrane 310 forms a layer over a layer 311 of carried substance molecules 302. The carried substance molecules 302 are positioned by one of several different methods. The first method, as previously discussed, involves dipping rigid portion 380 into a solution of the carried substance and allowing the solution to dry and form the layer. Micropore membrane 310 is then applied over the dried carried substance layer. Another method involves injecting the carried substance through port 312 of the semi-rigid portion with the micropore membrane already positioned on the surface of the probe. The injected carried substance forms a layer between the micropore membrane and surface 304 of the probe.

Returning the reader's attention to FIG. 2, the probe provides the medium to introduce heat energy into the tumor environment. Within the semi-rigid portion 380 of the probe is a cylindrical, thermally conductive plastic (preferably polycarbonate) tube 388 around which a resistive heater element wire 390 is wound and in which an accurate thermistor 392 is positioned. The resistive heating element directly heats the thermistor through the conductive material of tube 388. The heating element and thermistors 392 and 393 are connected to the external control system circuitry by a plurality of insulated electrical conductor wires 201 which extend through the semi-rigid and flexible portions to the end connector portion 384. More specifically, heater 390 has one end connected to connector terminal 384a and another end connected to terminal 384b. Thermistor 392 has one lead connected to terminal 384c and another lead connected to terminal 384d. Thermistor 393 has one lead connected to terminal 384d and another lead connected to terminal 384e.

Approximate typical probe dimensions which have been found useful in brain tissue are as follows: 9-12 cm for the semi-rigid portion, 5 cm for the flexible portion, 1-10 cm for the heater coil, and 2.2 mm for probe outer diameter.

The semi-rigid outersheath portion 380 of the probe is constructed of high-density polyethylene material or other suitably conductive material because of the need for heat transfer and temperature response. The semi-rigid portion also buffers the heat passing through allowing a more uniform heat distribution across the outer surface to reduce the effects of wire-wound heaters. The thermal buffer effect of the outer sheath further protects blood vessels and tissue from high temperatures. As the heat transfer away from the outer sheath increases, the temperature of the outer surface decreases with respect to the heater temperature. In such case as where a major blood vessel is adjacent to the probes, excessive heat will not be conducted to the flowing blood, because the heat transfer will be limited by the outer sheath. However, within normally perfused or typical tumor tissue the surface temperature is elevated and can be carefully controlled. The surface temperature can be calculated from the power delivered and the physical properties of the probe. More specifically, the perfusion is calculated from the measured power delivered to the heater element and the measured temperature from the thermistor.

The coated probes are stereotaxically placed in the tumor in a predetermined pattern for volumetric heating, with an imaging system being used for guidance in the placement of probes. In this regard, it should be noted that the preferred embodiment of the present invention is described here in terms of a method and apparatus for producing both a hyperthermia and a thermally elevated drug treatment within the brain, but that the invention may be also applicable to the neck, the chest cavity, the long bones of the body, or to other points of interest, including those not easily accessible because of overlying bones or delicate organs. Image-based stereotaxic placement of the probes is performed with an imaging system of the type having a gantry with a horizontal, cylindrical throat axially aligned with a movable patient cradle. A computerized tomography (CT) scanner is a well known form of such an imaging system and will therefore be used as a reference herein for the description of the preferred embodiment, although other imaging systems and techniques may be used, such as X-ray film, X-ray fluoroscopy, magnetic resonance imaging, electromagnetic imaging and ultrasound.

Figure 4:
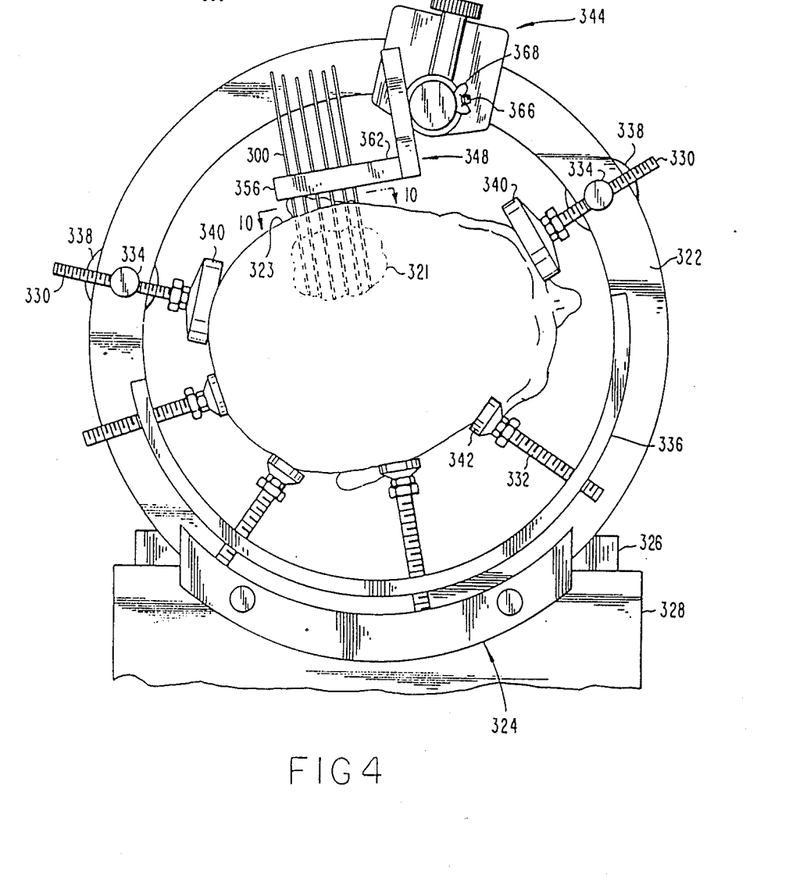
FIG. 4 shows a head end view of a patient lying on a patient cradle with a support frame in place for use in stereotaxic placement of probes according to the preferred embodiment of the present invention.
Figure 5:
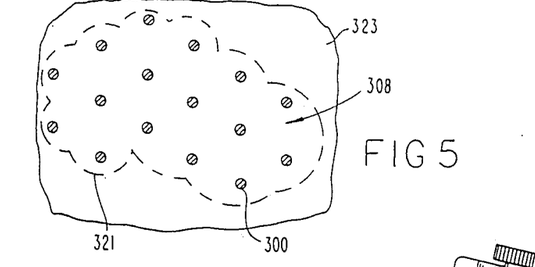
FIG. 5 is a sectional view taken along the lines 10-10 of FIG. 4.

FIG. 4 shows a head end view of a patient lying on a patient cradle with a support frame in place for use in stereotaxic placement of probes according to the present invention. In the illustrated view, six probes 300 are visible extending into a brain tumor 321. Ten other probes are hidden from view in the background of FIG. 4, for a total of 16 probes in this example, as shown in FIG. 5, which is a sectional view taken along lines 10—10 of FIG. 4, i.e., an axial view of the array of probes 300. Only the skull portion 323 immediately surrounding the tumor mass 321 is shown in the drawing. FIG. 5 illustrates the preferred probe pattern for volumetric heating of the illustrated tumor 321. As used herein, volumetric heating means heating an entire volume of a target mass above a minimum temperature.

Figure 6:
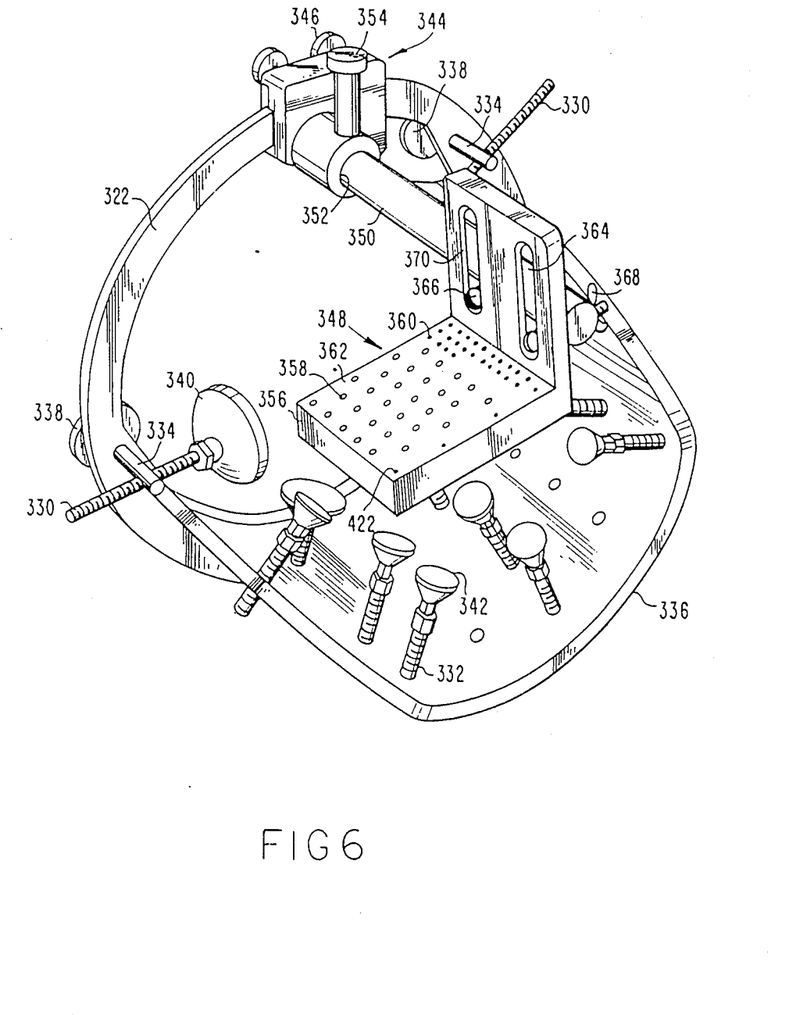
FIG. 6 is a perspective view of the support frame shown in FIG. 4.

The support frame for the patient's head includes a ring-like member or ring 322 encircling the head and clamped on its lower end to a ring mount generally designated 324. An adapter 326 mounts ring mount 324 to the head end 328 of the patient cradle. The details of the structure for mounting the ring frame to the patient cradle are disclosed in U.S. Pat. No. 4,360,028, which patent is hereby incorporated by reference. With combined reference to FIG. 4 and to FIG. 6, which shows a perspective view of the support frame, the support frame includes upper support rods 330 and lower support rods 332 mounted to ring 322 by spacers 334 and plastic shell 336, respectively. Upper support rods 330 are threadably engaged in spacers 334 which are mechanically linked to knobs 338. Each upper support rod 330 has a plastic cushion 340 pivotally mounted on one end. Patient support rods 332 each have a threaded shaft threadably engaged in shell 336 and a cone-shaped cushion 342 mounted on one end as shown. The support frame also includes a template carriage 344 slidably mounted on ring 322. Two tension knobs 346 are provided for clamping carriage 344 in a desired position on ring 322. A template 348 is mounted on a tubular extension arm 350 rotatably and slidably mounted in a bore 352 extending through template carriage 344 in a direction perpendicular to the plane of ring 322. Tension knob 354 is provided to lock extension arm 350 in a desired position within bore 352. Template 348 includes a main template block 356 formed of a radiolucent material and provided with an array of holes 358 for probe guidance and a set of holes 360 for optically coded identification of the orientation of the template in any particular image produced by the imaging system. Holes 358 and 360 all extend through template block 356 in a direction perpendicular to the top surface 362 thereof. Template 348 further includes a pair of slots 364 for vertical movement of template 348 with respect to tubular extension arm 350, the template being secured to extension arm 350 with a pair of bolts 366 and a pair of wing nuts 368 attached respectively thereto, each of the slots being provided with a seat 370 to restrain the head of bolt 366. In operation, after a patient has been placed on the patient cradle in a desired position with the head oriented, supported and restrained in a desired manner in the support frame, template 348 is moved into a desired position and orientation with respect to a tumor by adjustment of template carriage 344 on ring 322 and of tubular extension arm 350 within bore 352 of template carriage 344 and adjustment of the position of bolts 366 in slots 364 of the template. When the template is positioned, it is used as a guide for drilling entry holes through the patient's skull in line with predetermined locations in the tumor to be treated, and then a probe is interstitially implanted by insertion through each of the drilled holes.

When the probe has been interstitially implanted within the brain tumor, the carrier substance coating on the probe releases the drug from the carrier to the tissue when the carrier reaches a predetermined temperature above normal tissue temperature. The drug when released provides a treatment of the neoplastic cells included in the tumor tissue. The control system of the hyperthermia system energizes the heater element of the probe for heating the probe and carrier substance. The heat from the heater element then provides a second treatment of the neoplastic cells. Dependent on the selection of the carrier substance coating, the drug may also be released in response to the interstitial fluid of the tumor and the heat from the heater element. Both methods may be used in combination to release the drug from the carrier substance over a given period of time. To elevate the temperature of the drug and thereby increase its effectiveness level, the heater element of the probe is energized to heat not only the tissue but the therapeutic drug as well. Furthermore, the carrier substance also responds by releasing the therapeutic drug over a shorter period of time. In addition, heating the tissue increases the susceptibility of the tissue to the carried substance. Elevating the tissue temperature also increases the cellular metabolic rate and, therefore, increases the effectiveness and the effects of the carried substance.

By monitoring the temperature of the probe and surrounding environment along with the power delivered to the probe, a minimum temperature is maintained throughout the surrounding volume including the tissue. By regulating the temperature of the probes, the duration of heat application, or a combination of both, a graded release of the carried molecules is obtained along with maintaining the temperature of the treated tissue at a minimum level.

Figure 7:
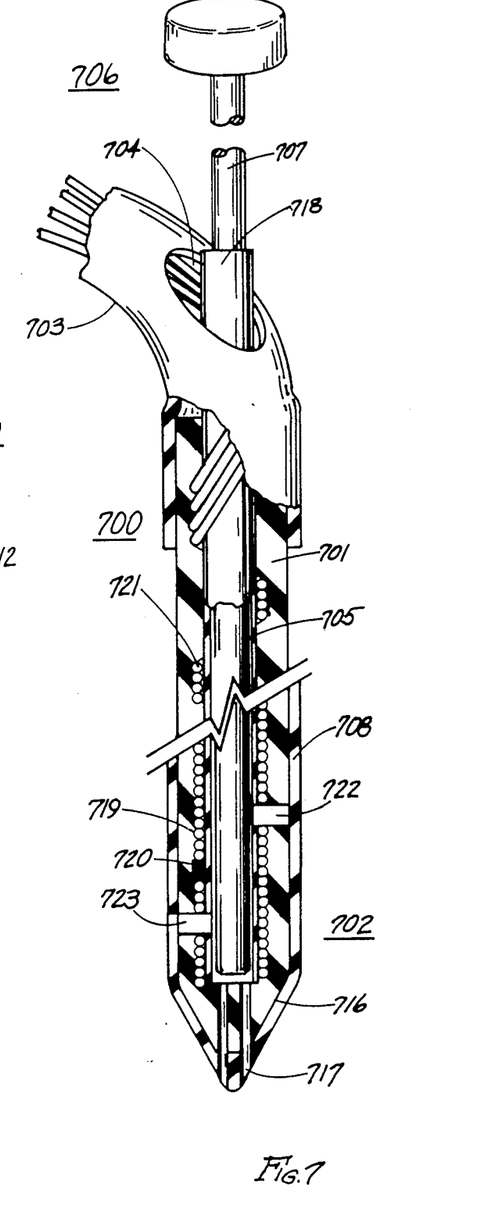
FIG. 7 is a view of illustrative apparatus of the present invention.

Depicted in FIG. 7 is apparatus 700 for treating tissue with first and second modalities for providing respective first and second treatments of surrounding tissue (not shown). Similar to probe 101, the apparatus includes a semi-rigid elongated member portion 701 which has a distal end 702 for implanting the member interstitially into the tissue. The probe has a flexible portion 703 with an aperture 704 therein for inserting a trocar stylet 707 into hollow passageway 705. The hollow passageway is longitudinally positioned within the elongated member and extends from the distal end 702 to the proximal end 706 of the probe. Flexible portion 703 is bent allowing the trocar stylet 707 to be inserted through the aperture into the hollow passageway of the member. When inserted, the stylet is utilized for implanting the semi-rigid portion interstitially into the tissue. Tip 716 of the probe at the distal end has been tapered to penetrate the tissue while minimizing distortion of the tissue and injury to the blood vessels. Tip 716 has a plurality of cylindrical ports 717 for delivering a drug from hollow passageway 705 directly to the tissue. Alternatively, side ports 722 and 723 are provided for injecting a drug or therapeutic agent between coating layer 708 and semi-rigid portion 701 as previously described.

When the elongated member has been interstitially implanted in the tissue, trocar stylet 707 is removed from the hollow passageway to permit the insertion or activation of a first modality for providing a first treatment of the tissue. The first modality comprises any one of a number of different treatments including radiation therapy, hyperthermia, or chemotherapy. A second modality is positioned about the distal end of the elongated member. This second modality comprises an outer or coating layer 708 including a carrier and a carried substance as previously described. The carrier substance transports molecules of the carried substance such as a chemotherapeutic drug within its molecular structure and also adheres to the outer surface of the semi rigid portion.

When the elongated member is implanted in the tissue, the carrier substance releases at a predetermined temperature, typically above 37° C., the carried substance to the tissue having, for example, neoplastic cancer cells. The release of the carried substance or the rate at which it is released is controlled by any one or more several factors including contact with the fluids of the tissue and the application of heat to the carrier substance produced by the first modality. The various forms and combinations of carried and carrier substances are those as described with respect to FIGS. 3(a)–(e).

The first modality is either integrated into the probe during manufacture or subsequently inserted into hollow passageway 705 after the probe is interstitially implanted. When integrated into the probe during manufacture, the first modality, for example, comprises a heater element for producing heat to provide a first treatment of the tissue as well as raise the temperature of the carrier substance when coating the outside of the probe. The heater element comprises a thermally conductive plastic tube 718, preferably commercially-available polyimide, around which a resistive heater element wire 719 is wound and on which an accurate thermistor 720 is positioned. A group of four conductors 721, which are loosely wrapped about the proximal end of semi-rigid portion 701, connects the heater wire and thermistor to connectors positioned at the connector portion of the probe (not shown), which is similar to connector portion 384 described with respect to probe 101. Two of the four wires connect to heater wires 719, whereas the other two conductors connect to thermistor 720. The semi-rigid material of the elongated member forms around the heater wire to insulate the wires from tissue fluid. The polyimide tube 718 insulates the heater and thermistor from any fluids that are passed through hollow passageway 705. When segment 703 is flexed, tube 718 extends through aperture 704 to permit the insertion of the trocar stylet 707.

A third modality for providing another treatment such as radiation therapy is also insertable in tube 718 through aperture 704.

Figure 8:
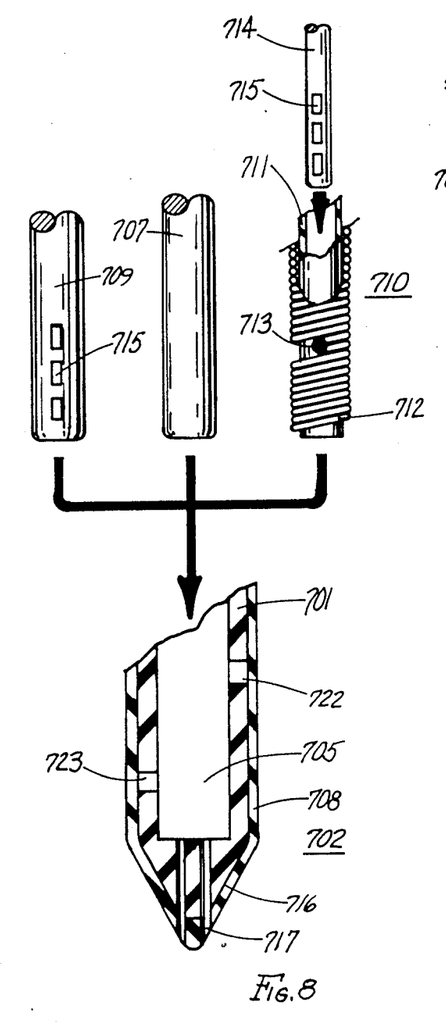
FIG. 8 is a view of another embodiment of the illustrative apparatus of this invention.

Alternatively, the elongated member is formed with hollow passageway 705 longitudinally positioned therein for subsequently positioning one or more modalities of treatment therein as shown in FIG. 8. One or more modalities of treatment and, similarly, trocar stylet 707 are insertable into hollow passageway 705. Trocar stylet 707 is initially positioned in the hollow passageway for implanting the distal end 702 of the probe interstitially into tissue. When the probe is implanted, the trocar stylet is removed, and one or more modalities are then positioned within the hollow passageway of the probe. One insertable modality is electrical heater element 710. Other insertable modalities include microwave and fluid heaters that are insertable into the hollow passageway.

The heater element comprises a semi-rigid hollow tube 711 such as polyimide or polycarbonate with a wire heater coil 712 tightly wound and affixed about the distal end thereof. A thermistor 713 is positioned on the tube within wire heater coil for sensing the temperature of the heater element and surrounding environment. A group of conductors (not shown) extends the length of tube 711 for connection to a connector manifold or directly to a heater control system (not shown) for applying current to the wire wound heater coil 712 and for determining the temperature sensed by thermistor 713. When energized, the wire wound heater coil produces heat for providing a hyperthermia treatment to the tissue surrounding the implanted probe as well as elevating the temperature of the carried substance of coating layer 708 for releasing the carried substance to the surrounding tissue. The heat produced by the first modality not only provides treatment of the tissue, but also increases the effectiveness level of the second modality such as the chemotherapeutic agent for treating the surrounding tissue.

Also depicted in FIG. 8 is an elongated insertable member 714 including a radiation source 715 such as a plurality of iridium seeds positioned within the member for providing a third modality of treatment. The insertable member is inserted in one of several different ways. First, the member is inserted in the hollow passageway 705 of electrical heater element 710 formed by tube 711 to provide a third modality of treatment. Alternatively, a larger diameter member 709 including radiation source 715 can be inserted directly into the hollow passageway of elongated member 701 for providing the first modality of treatment. In either case, the radiation source provides a well-known form of radiation treatment, commonly known as brachytherapy. The radiation source also elevates the effectiveness level of the chemotherapeutic agents within coating layer 708 surrounding the distal end of elongated member 701. Furthermore, when used in combination with the hyperthermia treatment of heater element 710, the two modalities also work in a synergistic manner to raise the effectiveness level of the hyperthermia treatment. All three modalities may be combined to provide a combined treatment whose total effectiveness level is greater than the sum total of each of the three modalities individually.

Depicted in FIG. 9 is a partial view of another embodiment of semi-rigid elongated member 900 of the present invention. As previously suggested, member 900 includes a hollow passageway 901 for positioning one or more modalities of treatment such as a heater element, radiation source, drug, etc. Surrounding the member is sheath 902 with a helical spacer 903 therebetween for forming passageway 904 about the member. The sheath includes a plurality of apertures 905 for passing an agent in passageway 904 to surrounding tissue (not shown) in which the member has implanted. The sheath includes side port 906 for injecting the agent such as a reactant or a therapeutic substance into passageway 904. The sheath comprises the same or similar material as member 900. Alternatively, the sheath may comprise a membrane for leeching an agent from passageway 904 to the surrounding tissue. Other sheating materials are contemplated dependent on the delivery method or system employed.

Similar in many respects to the probe described with respect to FIGS. 1 and 2, the apparatus of FIGS. 7, 8, and 9 provides a probe having a hollow passageway in which a heater element, a chemotherapeutic agent, and/or a source of radiation may be inserted after the probe is interstitially implanted in the affected tissue.

The elongated member 701 may be coated with any number of different chemotherapeutic agents or drugs and then inserted into a tumor for treatment thereof. The physician then selects another modality of treatment for insertion into the hollow passageway of the elongated member. In this manner, the apparatus associated with additional modalities of treatment may be selected and reused for subsequent treatments, thereby reducing the overall cost of the treatment.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. The carried and carrier substances have been described as forming one or more layers on the surface of the probe. However, the invention is not so limited. The carrier and carried substances may be integrated into semi-rigid portion 380 of the probe. Furthermore, the modalities of treatment may be combined in groups of two or more to meet the needs of individual patients as determined by the physician.

What is claimed is:

1. Apparatus for treating tissue, comprising:
    an elongated member interstitially implantable in said tissue and having a distal end for interstitially penetrating said tissue;
    a passageway longitudinally positioned in said member for positioning a first modality in said member, said first modality for providing a first treatment of said tissue; and
    a second modality positioned about said distal end and responsive to said first modality for providing a second treatment of said tissue.

2. The apparatus of claim 1 further comprising said first modality including a heater element insertable into said passageway for producing heat for said first treatment.

3. The apparatus of claim 2 wherein said second modality comprises a carried and a carrier substance joined with said elongated member, said carrier substance being responsive to said heat for releasing said carried substance for said second treatment.

4. The apparatus of claim 1 further comprising said first modality including a second elongated member insertable into said passageway and a source of radiation for said first treatment of said tissue.

5. The apparatus of claim 4 wherein said second modality includes a heater element positioned about said distal end for said second treatment.

6. The apparatus of claim 5 further comprising a drug joined with said distal end of said member and responsive to said heat for providing a third treatment of said tissue.

7. The apparatus of claim 4 wherein said elongated member includes an aperture for said passageway.

8. The apparatus of claim 7 further comprising a stylet insertable into said passageway through said aperture for implanting said elongated member interstitially in said tissue.

9. The apparatus of claim 4 wherein said second modality includes a drug joined with said elongated member for said second treatment.

10. The apparatus of claim 1 further comprising a third modality positioned about said distal end and responsive to at least one of said first and second modalities for providing a third treatment of said tissue.

11. The apparatus of claim 1 wherein said member includes an aperture for inserting a stylet into said passageway.

12. The apparatus of claim 1 further comprising a stylet insertable into said passageway for implanting said member interstitially in said tissue.

13. The apparatus of claim 1 wherein said member includes an aperture positioned about said distal end for delivering said first modality from said passageway to said tissue.

14. Apparatus for treating tissue comprising:
    an elongated member interstitially implantable in said tissue and having a distal end for interstitially penetrating said tissue;
    a passageway longitudinally positioned in said member for positioning a heater element therein, said heater element for producing heat; and
    a coating layer joined with said member about said distal end and responsive to said heat for releasing at a predetermined temperature above a temperature of said tissue a drug.

15. The apparatus of claim 14 further comprising said heater element.

16. A method for treating tissue with a first and a second modality of treatment, comprising:
    implanting an elongated member interstitially in said tissue;
    positioning said first modality in a passageway longitudinally positioned in said member; and
    responsive to said first modality, providing said second modality positioned about a distal end of said member when implanted interstitially in said tissue.

17. The method of claim 16 wherein said implanting comprises positioning a stylet in said passageway and inserting the distal end of said member interstitially in said tissue with said stylet positioned in said passageway.

18. The method of claim 17 wherein said positioning of said first modality includes removing said stylet from said passageway of said member when implanted in said tissue and positioning a heater element in said passageway for providing heat for said first modality.

19. The method of claim 18 further comprises positioning a source of radiation within a tube of said heater element, for providing a third modality of treatment.

20. The method of claim 18 wherein said providing includes releasing a drug at a temperature above a temperature of said tissue for said second modality in response to said heat from said first modality.

21. The method of claim 17 wherein said positioning of said first modality includes removing said stylet from said passageway of said member and positioning a source of radiation in said passageway.

22. Apparatus for treating tissue, comprising:
    an elongated member having a distal end for implanting said elongated member interstitially in said tissue;
    a passageway positioned longitudinally in said member;
    a stylet insertable into said passageway for implanting said member in said tissue;
    a heater element having a tube positioned therein and insertable into said passageway for producing heat for a first modality of treatment;

a second elongated member insertable into said tube and including a source of radiation for a second modality of treatment;

a coating layer joined with said member about said distal end responsive to said heat for releasing at a predetermined temperature above a temperature of said tissue a therapeutic substance for a third modality of treatment, the total effectiveness level of all of said modalities of treatment on said tissue being greater than the sum of each effectiveness level of said first, second, and third modalities individually.

23. Apparatus for treating tissue, comprising:

an elongated member interstitially implantable in said tissue and having a distal end for interstitially penetrating said tissue;

a passageway longitudinally positioned in said member for positioning a first modality in said member, said first modality for providing a first treatment of said tissue; and a second modality positioned about said distal end and interactive with said first modality for providing a second treatment of said tissue.

24. The apparatus of claim 23 further comprising a third modality positioned about said distal end and interactive with at least one of said first and second modalities for providing a third treatment.

* * * * *